United States Patent
Rozot et al.

(10) Patent No.: US 9,427,604 B2
(45) Date of Patent: Aug. 30, 2016

(54) USE OF BENZYLOXY-ETHYLAMINE DERIVATIVES AS A PRESERVATIVE, PRESERVATION METHOD, AND COMPOSITIONS

(75) Inventors: Roger Rozot, Lagny/Marne (FR); Maria Dalko, Versailles (FR)

(73) Assignee: L'OREAL, Paris (FR)

( * ) Notice: Subject to any disclaimer, the term of this patent is extended or adjusted under 35 U.S.C. 154(b) by 534 days.

(21) Appl. No.: 13/512,518

(22) PCT Filed: Nov. 25, 2010

(86) PCT No.: PCT/FR2010/052520
§ 371 (c)(1),
(2), (4) Date: Jul. 12, 2012

(87) PCT Pub. No.: WO2011/070264
PCT Pub. Date: Jun. 16, 2011

(65) Prior Publication Data
US 2012/0269740 A1    Oct. 25, 2012

Related U.S. Application Data

(60) Provisional application No. 61/287,378, filed on Dec. 17, 2009.

(30) Foreign Application Priority Data

Dec. 11, 2009  (FR) ..................... 09 58867

(51) Int. Cl.
*A61Q 17/00*  (2006.01)
*A61K 8/41*  (2006.01)
*A61Q 1/00*  (2006.01)
*A61Q 5/00*  (2006.01)
*A61Q 9/00*  (2006.01)
*A61Q 19/10*  (2006.01)

(52) U.S. Cl.
CPC ............. *A61Q 17/005* (2013.01); *A61K 8/41* (2013.01); *A61K 2800/524* (2013.01); *A61Q 1/00* (2013.01); *A61Q 5/00* (2013.01); *A61Q 9/00* (2013.01); *A61Q 19/10* (2013.01)

(58) Field of Classification Search
None
See application file for complete search history.

(56) References Cited

U.S. PATENT DOCUMENTS 5,714,155 A    2/1998  De Lacharriere et al.
6,521,239 B1 *  2/2003  Breton et al. ................. 424/401

FOREIGN PATENT DOCUMENTS

DE    2752253 A1 *  5/1979
EP    1496076 A1    1/2005
WO    WO-01/94322 A1   12/2001

OTHER PUBLICATIONS

Machine translation of DE 2752253, original document published May 1979.*
SciFinder record for DE 2752253, original document published May 1979.*
Lee et al. Biomacromolecules, 5 p. 877-882, 2004.*
Gufurov et al. Applied Biochemistry and Microbiology, 41(2), p. 213-218, 2005.*
Anonymous: "2-(benzyloxy)-1-ethanamine hydrochloride", Nov. 25, 2005, XP002580055, Retrieved from the Internet: URL: www.maybridger.com.
Anonymous: "2-(benzyloxy)ethanamine", 2006, XP002580056, Retrieved from the Internet: URL: www.chembridge.com.

* cited by examiner

*Primary Examiner* — Nissa Westerberg
(74) *Attorney, Agent, or Firm* — Polsinelli PC

(57) ABSTRACT

The invention relates to the use of a compound of formula (I), or salts thereof, as a preserving agent, in particular in a cosmetic, dermatological or pharmaceutical composition:

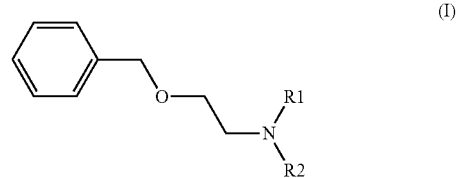

in which R1 and R2 represent H, methyl, ethyl, phenyl or benzyl.

The invention also relates to a method of preserving a cosmetic, dermatological or pharmaceutical composition, consisting in incorporating said compound of formula (I) therein; and also to the compositions thus obtained.

20 Claims, No Drawings

USE OF BENZYLOXY-ETHYLAMINE DERIVATIVES AS A PRESERVATIVE, PRESERVATION METHOD, AND COMPOSITIONS

CROSS REFERENCE TO RELATED APPLICATIONS

This application is a National Phase filing under 35 U.S.C. §371 PCT/FR2010/052520 filed on Nov. 25, 2010; and this application claims priority to Application No. 0958867 filed in France on Dec. 11, 2009, and this application claims the benefit of U.S. Provisional Application No. 61/287,378 filed on Dec. 17, 2009, under 35 U.S.C. §119; the entire contents of all are hereby incorporated by reference.

The present invention relates to the use of compounds of the family of benzyloxy-ethylamines as preserving agents, especially in cosmetic, dermatological or pharmaceutical compositions, and to said compositions.

It is common practice to introduce chemical preservatives into cosmetic or dermatological compositions, these preservatives being intended to combat the growth of microorganisms in these compositions, which would quickly make them unsuitable for use. It is in particular necessary to protect compositions against microorganisms capable of growing inside the composition and also against those which the user might introduce therein while handling it, in particular when taking up products in jars with the fingers.

The effectiveness of the preservatives conventionally used is variable and their formulation can pose problems of formulation, such as of incompatibility, or even of destabilization, in particular of emulsions. Furthermore, they may be the cause of undesirable side effects (irritation, allergy) in particular on sensitive skin. Thus, chemical preservatives commonly used are in particular parabens and formaldehyde-releasing compounds; but these preservatives have, however, the drawback of causing irritation, in particular on sensitive skin, when they are present at relatively high levels. Other known preservatives are organic hydroxy acids; but they may also give rise to irritation due to their desquamating effect on the skin, which is not always well tolerated.

Furthermore, the consumer, conscious of protecting the environment, increasingly seeks preservatives that are not environmentally hazardous.

There is thus still a need for preserving agents, in particular antimicrobial agents, whose activity is at least as effective as that of the compounds of the prior art, but which do not have the drawbacks of the latter.

One aim of the present invention is to propose novel preserving agents that have, in particular, a broad antimicrobial spectrum and that do not have the drawbacks of the prior art.

Thus, one subject of the present invention consists of the use of at least one compound of formula (I) as defined below, or a salt thereof, as a preserving agent. The expression "preserving agent" is understood to mean a substance that is commonly added to a composition in order to preserve said composition with respect to a contaminating agent. Advantageously, the compounds of formula (I) according to the invention are used as an antimicrobial and/or antibacterial and/or antifungal agent.

Another subject of the invention is a method for preserving a cosmetic, dermatological or pharmaceutical composition, characterized in that it consists in incorporating into said composition at least one compound of formula (I) or a salt thereof, as defined below.

Another subject of the invention is a cosmetic, dermatological or pharmaceutical composition comprising, in a physiologically acceptable medium, at least one compound of formula (I), or a salt thereof.

The Applicant has observed, surprisingly and unexpectedly, that the compounds of the family of benzyloxy-ethylamines of formula (I) have good antimicrobial properties, whether in respect to bacteria, yeasts or moulds.

Due to their broad antimicrobial spectrum, these compounds may therefore be used, in particular in cosmetic compositions, as antimicrobial agents, in particular as antibacterial agents, and/or as antifungal agents, i.e. anti-yeast and/or anti-mould agents. These compounds of formula (I) may therefore advantageously be used in cosmetic and/or dermatological compositions, in particular as a preserving agent.

To the Applicant's knowledge, the benzyloxy-ethylamines of formula (I) according to the invention have never been proposed in cosmetic compositions, let alone as a preserving agent.

The compounds of formula (I) according to the invention have the advantage of having a clearly defined and characterized chemical structure, resulting in easy reproducibility of their manufacture; their industrial feasibility is also relatively simple.

Furthermore, they have good solubility or compatibility with the media commonly used in cosmetics, especially aqueous media.

The compounds according to the invention therefore correspond to the formula (I) below:

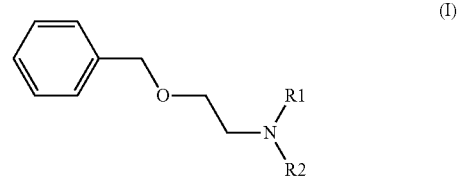

in which R1 and R2 represent, independently of one another, a hydrogen atom or a methyl, ethyl, phenyl or benzyl radical; and the salts thereof.

Preferably, R1 represents H.
Preferably, R2 represents H or benzyl.

The organic or mineral salts of the compounds of formula (I), are also part of the invention. The salified compounds therefore correspond to the formula (I'):

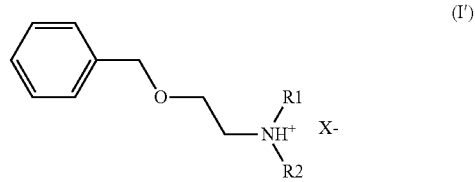

in which R1 and R2 are as defined in formula (I) and X— is an organic and/or mineral, cosmetically acceptable anion, or mixture of anions.

In particular, X— may represent an anion, or a mixture of anions, chosen from halides, in particular chloride, bromide, fluoride or iodide; a hydroxide; a phosphate; a sulphate; a hydrogen sulphate; alkyl sulphates in which the alkyl is a linear or branched $C_1$-$C_6$ alkyl, such as methyl sulphate or ethyl sulphate; carbonates and hydrogen carbonates; salts of carboxylic acids, such as formate, acetate, citrate, tartrate and oxalate; alkyl sulphonates in which the alkyl is a linear or branched $C_1$-$C_6$ alkyl, such as methyl sulphonate; aryl sulphonates in which the aryl, preferably phenyl, is optionally substituted with one or more $C_1$-$C_4$ alkyl radicals, for instance 4-tolyl sulphonate; alkyl sulphonates such as mesylate; and mixtures thereof.

As compounds of formula (I) according to the invention, mention may in particular be made of:

CAS 38336-04-8

CAS 10578-75-3

CAS 38336-06-0

CAS 38336-07-1

A mixture of compounds of formula (I) may, of course, be used.

Preferably, the composition does not comprise any preserving agents other than those of formula (I). In particular, the composition does not contain parabens.

Some of the compounds of formula (I) are available commercially, in particular from Maybridge for the compound of CAS 10578-75-3 or Chembridge for the compound of CAS 38336-04-8.

These compounds may be easily synthetized by a person skilled in the art, for example according to the following processes:

A/ The compounds in which R1=R2=H may be prepared in three steps from ethanolamine via the formation of an oxazoline intermediate. The opening of the latter by benzyl alcohol results in the formation of the N-acetylated compound. The deprotection of the acetate group may be carried out under conventional conditions, in particular with $H_3PO_4$ under reflux or under basic conditions.

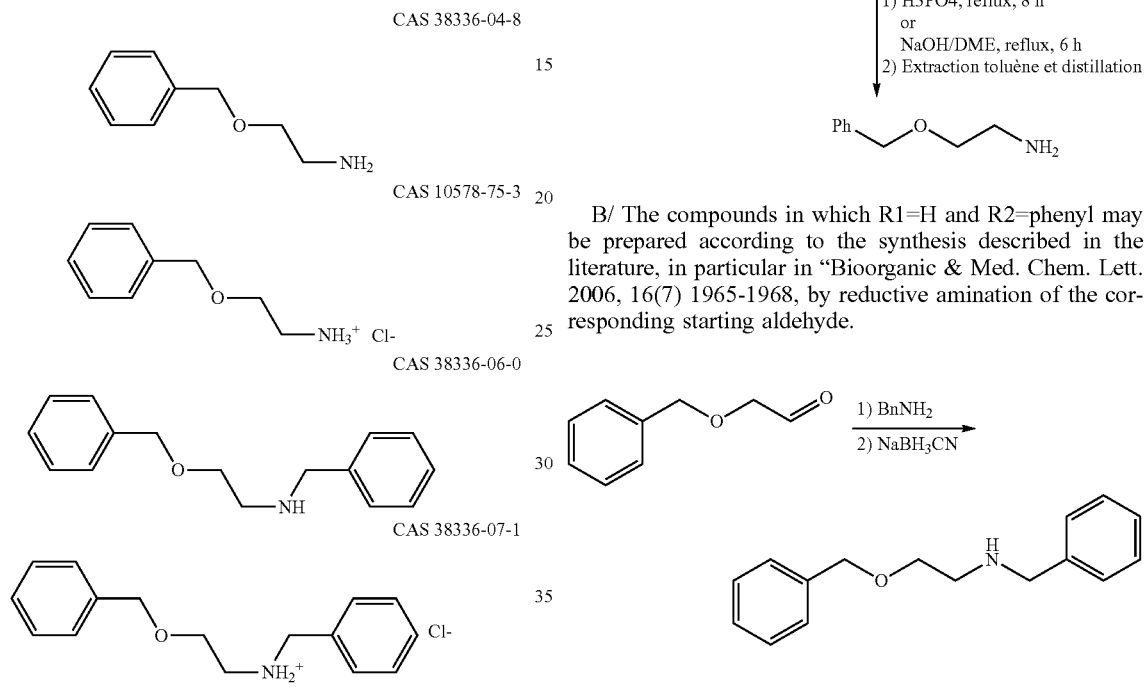

B/ The compounds in which R1=H and R2=phenyl may be prepared according to the synthesis described in the literature, in particular in "Bioorganic & Med. Chem. Lett. 2006, 16(7) 1965-1968, by reductive amination of the corresponding starting aldehyde.

The compounds of the family of benzyloxy-ethylamines of formula (I) according to the invention may be present in the cosmetic, dermatological or pharmaceutical compositions in an amount sufficient to obtain the desired effect, and represent in particular 0.1 to 5% by weight, preferably 0.25 to 3% by weight, and more particularly 0.5 to 2% by weight, of the total weight of the composition.

The compositions comprising the compounds of formula (I) according to the invention comprise a physiologically acceptable medium, i.e. a medium that is compatible with keratin materials such as facial or body skin, the lips, the hair, the eyelashes, the eyebrows and the nails.

They may be in any galenic form that is suitable for topical application, especially in the form of an aqueous, aqueous-alcoholic, organic or oily solution; a suspension or dispersion in solvents or fatty substances, of the lotion or serum type; in the form of a vesicular dispersion; in the form of a W/O, O/W or multiple emulsion such as a cream or a milk; in the form of an ointment, a gel, a solid stick, pasty or solid anhydrous products, a foam, especially an aerosol foam, or a spray.

The physiologically acceptable medium in which the compounds can be used, and also its constituents, their amount, the galenic form of the composition and the preparation method thereof may be chosen by those skilled in the art on the basis of their general knowledge as a function of the type of composition desired.

In particular, the composition may comprise any fatty substance normally used in the field of application envisaged. Mention may in particular be made of silicone fatty substances such as silicone oils, gums and waxes and also non-silicone fatty substances such as oils, pastes and waxes of plant, mineral, animal and/or synthetic origin. The oils may be volatile or non-volatile.

Mention may also be made of hydrocarbons, especially isoparaffins; synthetic esters and ethers comprising in total 8 to 60 carbon atoms; $C_8$-$C_{32}$ fatty alcohols and $C_8$-$C_{32}$ fatty acids.

The composition may also comprise an aqueous medium, an aqueous-alcoholic medium containing a $C_2$-$C_6$ monoalcohol such as ethanol or isopropanol, or an organic medium comprising standard organic solvents such as $C_2$-$C_6$ alcohols, in particular ethanol and isopropanol, glycols such as propylene glycol, and ketones.

The composition may comprise adjuvants that are common in the field under consideration, such as emulsifiers, surfactants, hydrophilic or lypophilic thickeners or gelling agents, active agents, in particular cosmetic active agents, antioxidants, fragrances, fillers, pigments, UV-screening agents, odour absorbers, dyes, moisturizers (glycerine), vitamins, essential fatty acids, polymers, especially liposoluble polymers, opacifiers, stabilizers, sequestrants, conditioners and propellants. Needless to say, a person skilled in the art will take care to select this or these adjuvants, and/or the amount thereof, such that the advantageous properties of the composition according to the invention are not, or are not substantially, adversely affected by the envisioned addition.

The pH of the compositions according to the invention, when they comprise at least one aqueous phase (for example aqueous solutions, emulsions), is preferably between 4 and 9, preferably between 4 and 7, advantageously from 5 to 6 and in particular is a pH of 5.5.

The composition according to the invention may in particular be in the form of:
- a product for making up the skin of the face, body or lips, such as a foundation, a face powder, an eye shadow, a concealer stick, a cover stick, an eyeliner, a mascara, a lipstick, a nail varnish or a nail care product;
- a sun protection composition or an artificial tanning composition;
- an aftershave gel or lotion;
- a hair-removing cream;
- a body hygiene composition such as a deodorant, a shower gel or a shampoo;
- a pharmaceutical composition;
- a solid composition such as a soap or a cleansing bar;
- an aerosol composition also comprising a pressurized propellant;
- a hairsetting lotion, a hair-styling cream or gel, a dye composition (in particular an oxidation dye composition), a hair-restructuring lotion, a permanent-wave composition, a lotion or a gel for combating hair loss; or
- a composition for buccodental use, for example a toothpaste.

The invention is illustrated in greater detail in the following exemplary embodiments.

Example 1

Determination of the Antimicrobial Activity of Compounds According to the Invention in Water The antimicrobial efficacy of compounds of formula (I) was evaluated via the challenge test or artificial contamination method after having introduced said compounds into water.

Compounds Tested

| | Structure | Source |
|---|---|---|
| Compound A | Ph-CH$_2$-O-CH$_2$CH$_2$-NH$_3^+$ Cl- | MO 07103 from the company Maybridge |
| Compound B | Ph-CH$_2$-O-CH$_2$CH$_2$-NH$_2^+$-CH$_2$-Ph Cl- | Prepared from the unsalified compound* |

*Synthesis of compound B: the unsalified compound (CAS 38336-06-0) is prepared according to the synthesis described in Bioorganic & Med. Chem. Letters (2006), 16(7), 1965-1968; this compound is then mixed with HCl (5N) in isopropanol, and the compound B is recovered by filtration, with a yield of 95%.

Protocol

The method of the challenge test consists of an artificial contamination of the sample with microbial strains from collection (bacteria, yeasts and moulds) and of an evaluation of the number of revivable microorganisms seven days after inoculation.

In order to demonstrate the effect of a compound of formula (I), the antimicrobial activity of an aqueous solution containing an amount "x" of said compound was compared with the same solution alone (control), after inoculation of approximately $10^6$ CFU (colony-forming units)/gram of aqueous solution.

Microorganism Cultures 5 pure cultures of microorganisms are used.

| MICROORGANISMS | Subculturing medium | T° | ATCC |
|---|---|---|---|
| *Escherichia coli* (Ec) | Trypto-casein soy | 35° C. | 8739 |
| *Enterococcus faecalis* (Ef) | Trypto-casein soy | 35° C. | 33186 |
| *Pseudomonas aeruginosa* (Pa) | Trypto-casein soy | 35° C. | 19429 |
| *Candida albicans* (Ca) | Sabouraud | 35° C. | 10231 |
| *Aspergillus niger* (An) | Malt | 35° C. | 6275 |

ATCC = American Type Culture Collection

The strains of gram−bacteria (*Escherichia coli* and *Pseudomonas aeruginosa*), gram+bacterium (*Enterococcus faecalis*), yeast (*Candida albicans*), and mould (*Aspergillus niger*) are inoculated into subculturing medium, respectively the day before inoculation for the bacteria and the yeast, and 5 days before inoculation for the mould.

On the day of inoculation:
- a suspension in tryptone salt diluent is prepared, respectively, for the bacteria and the yeast, so as to obtain by spectrophotometer a suspension with an optical density of between 35% and 45% of transmitted light at 544 nm;
- for the mould, the spores are collected by washing the agar with 6 to 7 ml of harvesting solution and the suspension is recovered in a sterile tube or flask.

After having homogenized the microbial suspension, 0.2 ml of inoculum (the suspensions are used pure: between $1 \times 10^8$ and $3 \times 10^8$ CFU per ml) are placed in each pill bottle and the microbial suspension is completely homogenized in the 20 g of product (=aqueous solution containing the compounds of formula (I) at the concentrations indicated) using a spatula.

The content of microorganisms present in the product corresponds after homogenization to a concentration of $10^6$ microorganisms per gram of product, i.e. inoculation to 1% of an inoculum containing $10^8$ microorganisms per ml.

After 7 days of contact time between the microorganisms and the product at 22° C.±2° C. and in the dark, ten-fold dilutions are carried out and the number of revivable microorganisms remaining in the product is counted.

Results

|  | Content | final pH | No. of CFU/gram of product at T7 days (inoculation level at $10^6$ microorganisms/g) | | | | |
|---|---|---|---|---|---|---|---|
|  |  |  | E. coli | P. aeruginosa | E. faecalis | C. albicans | A. niger |
| Compound A | 1% | 7.5 | <200 | <200 | <200 | <200 | $3.6 \times 10^4$ |
| Compound A | 0.75% | 7.4 | <200 | <200 | <200 | $5.8 \times 10^3$ | $1.6 \times 10^5$ |
| Compound A | 0.5% | 7.4 | <200 | <200 | <200 | $1.3 \times 10^6$ | $6.2 \times 10^5$ |
| Compound A | 0.25% | 6.9 | $2.8 \times 10^3$ | $3.0 \times 10^3$ | $1.2 \times 10^3$ | $2.3 \times 10^6$ | $1.0 \times 10^6$ |
| Compound A | 0.1% | 7.2 | $1.9 \times 10^6$ | $1.5 \times 10^5$ | $6.9 \times 10^4$ | $2.8 \times 10^6$ | $1.0 \times 10^6$ |
| Compound A | 0.05% | 7 | $6.2 \times 10^6$ | $1.9 \times 10^6$ | $3.3 \times 10^5$ | $3.0 \times 10^6$ | $1.3 \times 10^6$ |
| Compound A | 0.01% | 7 | $7.4 \times 10^6$ | $9.0 \times 10^6$ | $4.1 \times 10^5$ | $3.2 \times 10^6$ | $1.4 \times 10^6$ |
| Compound B | 1% | 6.6 | <200 | <200 | <200 | <200 | <200 |

<200 CFU: sensitivity threshold of the method

This study shows that the compounds of formula (I) according to the invention have a very broad antimicrobial spectrum due to their antibacterial and fungal activity. They are effective preservatives, in particular in the aqueous solutions tested.

Example 2

A lotion is prepared, comprising (% by weight):

| | |
|---|---|
| compound A | 1% |
| glycerol | 2% |
| ethyl alcohol | 20% |
| oxyethylenated (26 OE) oxypropylenated (26 OP) butanol, oxyethylenated (40 OE) hydrogenated castor oil in water | 1% |
| demineralized water | qs 100% |

Example 3

A facial gel is prepared, comprising (% by weight):

| | |
|---|---|
| compound A | 1% |
| glyceryl polyacrylate (Norgel) | 30% |
| polyacrylamide/C13-14 isoparaffin/laureth-7 (Sepigel 305) | 2% |
| silicone oil | 10% |
| water | qs 100% |

Example 4

A treating gel is prepared, comprising (% by weight):

| | |
|---|---|
| compound B | 1% |
| xanthan gum | 1% |
| glycerol | 2% |
| ethanol | 20% |
| mixture of oxyethylenated (26 OE) and oxypropylenated (26 OP) butyl alcohol, oxyethylenated (40 OE) hydrogenated castor oil in water | 1% |
| fragrance | qs |
| demineralized water | qs 100% |

Example 5

A foaming cleansing cream is prepared, comprising (% by weight):

| | |
|---|---|
| ethylene glycol monostearate | 2% |
| compound B | 0.5% |
| magnesium aluminium silicate hydrate | 1.7% |
| hydroxypropyl methyl cellulose | 0.8% |
| mixture of sodium cocoyl isethionates and coconut fatty acids (Elfan AT 84 G from Akzo) | 15% |
| stearic acid | 1.25% |
| sodium lauroyl sarcosinate at 30% in water | 10% |
| fragrance | qs |
| demineralized water | qs 100% |

Example 6

A care cream is prepared, comprising (% by weight):

| | |
|---|---|
| sorbitan tristearate | 1% |
| compound A | 1.5% |
| crosslinked carboxyvinyl homopolymer | 0.4% |
| xanthan gum | 0.5% |

-continued

| | |
|---|---|
| ethylene glycol dimethacrylate/lauryl methacrylate copolymer | 1% |
| cyclopentadimethylsiloxane | 6% |
| glycerol | 3% |
| emulsifier | 4% |
| fragrance | qs |
| demineralized water | qs 100% |

Example 7

A cover stick is prepared, comprising (% by weight):

| | |
|---|---|
| waxes (carnauba wax and ozokerite) | 14% |
| liquid fraction of shea butter | 4% |
| titanium and zinc oxides | 22% |
| iron oxides | 4% |
| compound A | 1% |
| polydimethylsiloxane/hydrated silica | 0.1% |
| cetyl alcohol | 1.4% |
| isoparaffin | qs 100% |

Example 8

A tinted cream is prepared, comprising (% by weight):

| | |
|---|---|
| hydrogenated lecithin | 2.4% |
| apricot kernel oil | 6% |
| ethylene glycol dimethacrylate/lauryl methacrylate copolymer | 1% |
| oxyethylenated (5 OE) soybean sterols | 1.6% |
| compound B | 1% |
| iron oxides | 0.9% |
| titanium oxide | 5% |
| polyacrylamide/$C_{13}$-$C_{14}$ isoparaffin/laureth-7 (Sepigel 305) | 4% |
| cyclopentadimethylsiloxane | 6% |
| glycerol | 6% |
| propylene glycol | 6% |
| fragrance | qs |
| demineralized water | qs 100% |

The invention claimed is:

1. A method for preserving a cosmetic, dermatological or pharmaceutical composition, which comprises incorporating into said composition as preserving agent at least one compound of formula (1) or a salt thereof

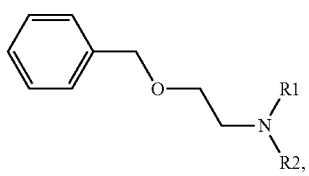

(I)

in which R1 is a hydrogen atom and R2 is a hydrogen atom or a benzyl radical.

2. A cosmetic, dermatological or pharmaceutical composition comprising, in a physiologically acceptable medium, at least one compound of formula (1), or a salt thereof:

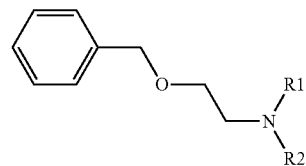

(I)

in which R1 is a hydrogen atom and R2 is a hydrogen atom or a benzyl radical;

the compound of formula (1) and/or a salt thereof, alone or as a mixture, being present in an amount between 0.1 and 5% by weight, of the total weight of the composition.

3. The composition according to claim 2, in which the at least one compound of formula (1) is salified and correspond to the formula (1'):

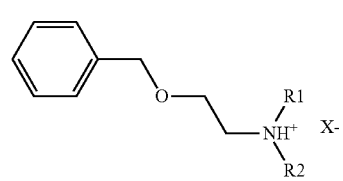

(1')

in which R1 is a hydrogen atom and R2 is a hydrogen atom or a benzyl radical; and X— is an organic and/or mineral, cosmetically acceptable anion, or mixture of anions.

4. The composition according to claim 2, in which the compound of formula (1) or a salified form of (1) is chosen from:

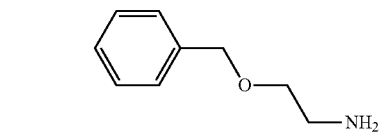

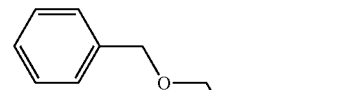

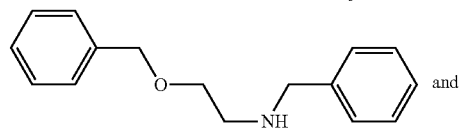

and

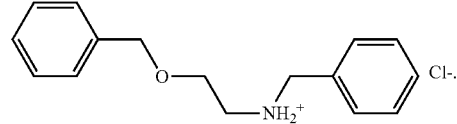

5. The composition according to claim 2, in which the compound of formula (1) and/or a salt thereof, alone or as a mixture, is present in an amount between 0.25 and 3% by weight of the total weight of the composition.

6. The composition according to claim 2, in which the physiologically acceptable medium comprises at least one ingredient chosen from: silicone fatty substances; non-silicone fatty substances; an aqueous medium; an aqueous-alcoholic medium containing a $C_2$-$C_6$ monoalcohol; $C_2$-$C_6$ alcohols, glycols; ketones; emulsifiers, surfactants, hydrophilic or lypophilic thickeners or gelling agents, and active agents.

7. The composition according to claim 2, which is in the form of:
a product for making up the skin of the face, body or lips;
a sun protection composition or an artificial tanning composition;
an aftershave gel or lotion;
a hair-removing cream;
a body hygiene composition;
a pharmaceutical composition;
a solid composition;
an aerosol composition also comprising a pressurized propellent;
a hairsetting lotion, a hair-styling cream or gel, a dye composition; or
a composition for buccodental use.

8. The composition according to claim 5, in which the compound of formula (1) or a salified form of (1) is chosen from:

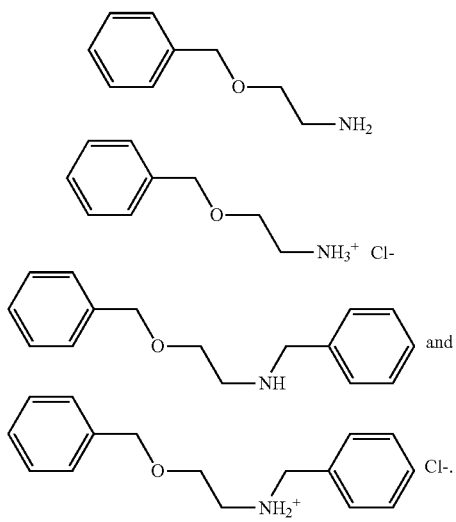

9. The composition according to claim 3, in which the compound of formula (1) and/or a salt thereof, alone or as a mixture, is present in an amount between 0.25 and 3% by weight of the total weight of the composition.

10. The composition according to claim 4, in which the compound of formula (1) and/or a salt thereof, alone or as a mixture, is present in an amount between 0.25 and 3% by weight of the total weight of the composition.

11. The composition according to claim 2, in which the compound of formula (1) and/or a salt thereof, alone or as a mixture, is present in an amount between 0.5 and 2% by weight of the total weight of the composition.

12. The composition according to claim 6, in which the compound of formula (1) and/or a salt thereof, alone or as a mixture, is present in an amount between 0.25 and 3% by weight of the total weight of the composition.

13. The composition according to claim 7, in which the compound of formula (1) and/or a salt thereof, alone or as a mixture, is present in an amount between 0.25 and 3% by weight of the total weight of the composition.

14. The composition according to claim 3, in which the compound of formula (1) and/or a salt thereof, alone or as a mixture, is present in an amount between 0.5 and 2% by weight of the total weight of the composition.

15. The composition according to claim 4, in which the compound of formula (1) and/or a salt thereof, alone or as a mixture, is present in an amount between 0.5 and 2% by weight of the total weight of the composition.

16. The composition according to claim 6, in which the compound of formula (1) and/or a salt thereof, alone or as a mixture, is present in an amount between 0.5 and 2% by weight of the total weight of the composition.

17. The composition according to claim 7, in which the compound of formula (1) and/or a salt thereof, alone or as a mixture, is present in an amount between 0.5 and 2% by weight of the total weight of the composition.

18. The method according to claim 1, in which the at least one compound of formula (1) is salified and correspond to the formula (1'):

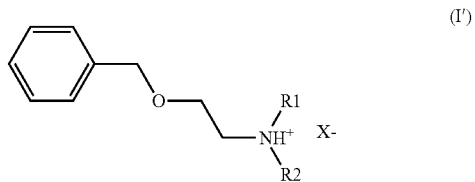

in which R1 is a hydrogen atom and R2 is a hydrogen atom or a benzyl radical; and X— is an organic and/or mineral, cosmetically acceptable anion, or mixture of anions.

19. The method according to claim 1, in which the compound of formula (1) or a salified form of (1) is chosen from:

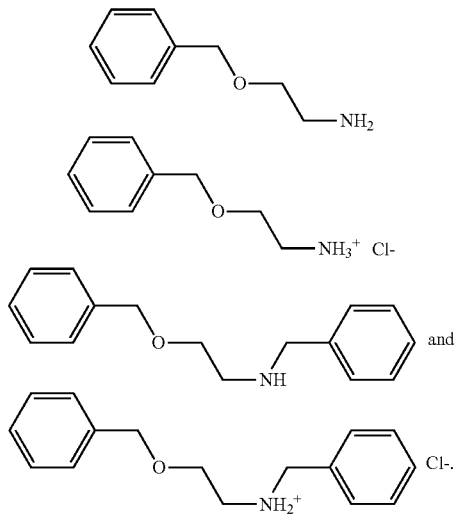

20. The method according to claim 1, in which the compound of formula (1) and/or a salt thereof, alone or as a mixture, is present in an amount between 0.25 and 3% by weight of the total weight of the composition.

* * * * *